United States Patent
Feiler et al.

(10) Patent No.: US 8,088,109 B2
(45) Date of Patent: Jan. 3, 2012

(54) METHOD AND APPARATUS FOR PROVIDING IMMEDIATE SUPPLEMENTAL BLOOD FLOW TO AN ORGAN

(75) Inventors: Ernest Feiler, Lafayette, CO (US); Warren Roh, Monument, CO (US); Eckehart Zimmermann, Monument, CO (US)

(73) Assignee: Surgical Pioneering, LLC, Layfayette, CO (US)

( * ) Notice: Subject to any disclaimer, the term of this patent is extended or adjusted under 35 U.S.C. 154(b) by 31 days.

(21) Appl. No.: 11/900,366

(22) Filed: Sep. 11, 2007

(65) Prior Publication Data
US 2008/0058850 A1 Mar. 6, 2008

Related U.S. Application Data

(63) Continuation-in-part of application No. 11/057,613, filed on Feb. 14, 2005.

(51) Int. Cl.
*A61B 17/32* (2006.01)
(52) U.S. Cl. .................................................. 604/184
(58) Field of Classification Search ............... 600/562, 600/566–567; 606/167, 170, 172, 179, 184–185
See application file for complete search history.

(56) References Cited

U.S. PATENT DOCUMENTS

| | | | | |
|---|---|---|---|---|
| 5,375,603 A * | 12/1994 | Feiler | | 600/474 |
| 5,377,116 A * | 12/1994 | Wayne et al. | | 700/175 |
| 5,423,330 A * | 6/1995 | Lee | | 600/566 |
| 5,871,495 A * | 2/1999 | Mueller | | 606/185 |
| 6,152,918 A * | 11/2000 | Padilla et al. | | 606/15 |
| 6,251,121 B1 * | 6/2001 | Saadat | | 606/180 |
| 6,447,539 B1 * | 9/2002 | Nelson et al. | | 623/1.11 |
| 6,482,220 B1 * | 11/2002 | Mueller | | 606/174 |
| 7,340,309 B2 * | 3/2008 | Miazga et al. | | 607/115 |
| 2001/0027317 A1 * | 10/2001 | Goble | | 606/41 |
| 2003/0040765 A1 * | 2/2003 | Breznock | | 606/184 |
| 2004/0191116 A1 * | 9/2004 | Jarvik et al. | | 422/44 |
| 2004/0215072 A1 * | 10/2004 | Zhu | | 600/407 |

* cited by examiner

*Primary Examiner* — S. Thomas Hughes
*Assistant Examiner* — Ashley Cronin
(74) *Attorney, Agent, or Firm* — Law Office of Dale B Halling

(57) ABSTRACT

The system and method creates immediate supplemental blood flow into an organ by punching a cannula into the organ to remove a core of the organ. The process of punching creates essentially no heat and therefore does not cauterize the wound. In the case of the heart this results in immediate supplemental blood flow into the heart muscle. Animal tests have shown this immediate blood flow is sufficient to sustain the heart even when a major coronary artery is completely blocked. The procedure may be performed in an open surgical field procedure by punching cores from the outside of the heart in or it may be a percutaneous catheter procedure punching cores from the inside-out of an organ.

14 Claims, 6 Drawing Sheets

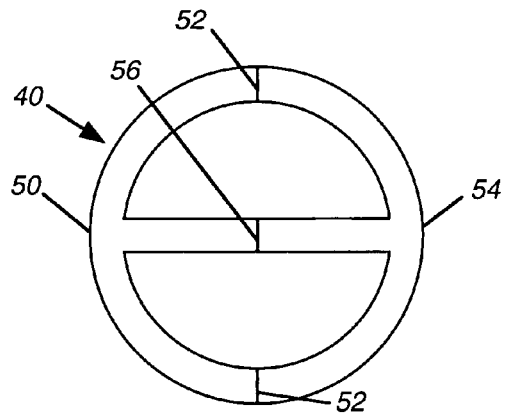
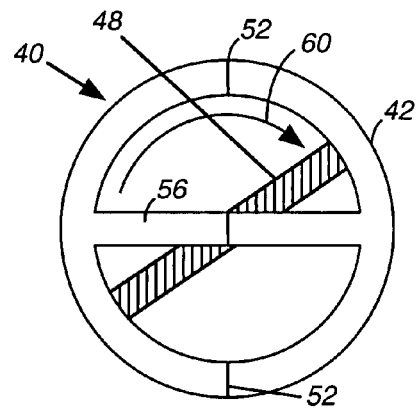
FIG. 5  FIG. 6
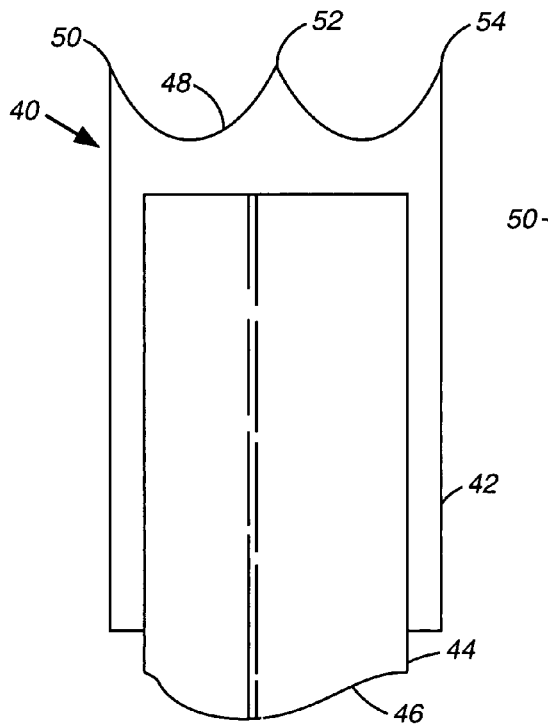
FIG. 3
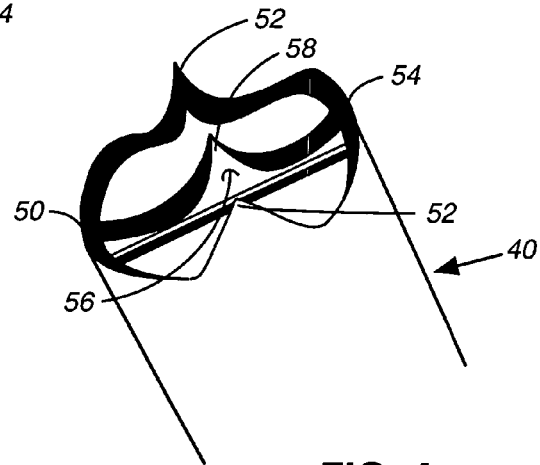
FIG. 4

US 8,088,109 B2

METHOD AND APPARATUS FOR PROVIDING IMMEDIATE SUPPLEMENTAL BLOOD FLOW TO AN ORGAN

RELATED APPLICATIONS

The present invention is a continuation-in-part of the U.S. patent application, application Ser. No. 11/057,613, filed on Feb. 14, 2005, entitled "Trans-Myocardial Fluid-Jet Revascularization Arrangement" and is hereby incorporated by reference.

STATEMENT REGARDING FEDERALLY SPONSORED RESEARCH

Not Applicable

THE NAMES OF THE PARTIES TO A JOINT RESEARCH AGREEMENT

Not Applicable

REFERENCE TO A SEQUENCE LISTING, A TABLE, OR A COMPUTER PROGRAM LISTING

Not Applicable

BACKGROUND OF THE INVENTION

Coronary artery bypass graft surgery consists of bringing blood from a source of normal arterial pressure through grafts that are attached to the coronary arteries where they have been surgically opened beyond the obstructed area. If the coronary arteries are too small or too severely diseased for such surgery, they are also too small for balloon dilation and stent insertion. Therefore, these patients are left with incomplete revascularizations. This can lead to subsequent need for re-operation for angina pain, heart attacks, rhythm disturbances or death.

Coronary arteriograms show only the larger arteries, and cannot show vascular disease in small arteries. Therefore, incomplete revascularization cannot be recognized when it is due to small arterial branch obstructions often frequently present in diabetics, but also elderly people, and patients after a heart attack.

In areas of inadequate perfusion as above, mechanical methods were attempted to make ventriculo-myocardial channels using primarily cannulas or trocars. They failed apparently because they produced slits instead of channels.

A system using lasers to create ventriculo-myocardial channels was used more successfully and transiently the recognized alternative surgical approach when coronary bypass grafting and balloon angioplasty was not possible. Unfortunately the laser channels frequently closed as well. The closure of these channels is postulated to be due to the high temperature generated by the laser which causes burned channel walls with subsequent scarring and closure.

Other revascularization techniques have been proposed. One involves boring holes in the heart muscle. The boring is designed to generate heat and cauterize the wound. The heart will then generate new arteries and veins around the channel wall. The heart, it is postulated, will then generate new arteries and veins around the cauterized channels, a process referred to as angioneogenesis. This procedure does not provide immediate supplemental blood flow to the heart or other organ during surgery, making it impossible to predict success.

Thus there exists a need for a procedure that provides immediate supplemental blood flow to the heart or other organ when bypass grafts or balloon angioplasty cannot be performed.

BRIEF SUMMARY OF INVENTION

The present invention relates to a method and apparatus for providing immediate supplemental blood flow into the heart or other organ as well as the diagnostic tools associated with the procedure. The present invention overcomes the problems of the prior art by punching a cannula into the organ to remove a core of the organ. The process of punching creates essentially no heat and therefore does not cauterize the wound. In the case of the heart this results in immediate blood flow into the heart muscle. Animal tests have shown that this immediate supplemental blood flow is sufficient to sustain the heart even when a major coronary artery is completely blocked. The procedure may be performed in an open heart surgery method, punching cores from the outside of the heart in or may be a percutaneous catheter procedure punching cores from the inside-out.

BRIEF DESCRIPTION OF THE SEVERAL VIEWS OF THE DRAWINGS

FIG. 3 is a cutaway view of a percutaneous cannula in accordance with one embodiment of the invention; and FIG. 4 is a top left perspective view of a percutaneous cannula in accordance with one embodiment of the invention;

FIG. 5 is a top view of a percutaneous cannula in accordance with one embodiment of the invention;

FIG. 6 is a top view of a percutaneous cannula in accordance with one embodiment of the invention;

DETAILED DESCRIPTION OF THE INVENTION

The present invention relates to a method and apparatus for providing immediate supplemental blood flow to an organ and the related diagnostic techniques. The present invention overcomes the problems of the prior art by punching a cannula with suction into the organ to remove a core of the channel that has been created in that organ. The process of punching creates essentially no heat and therefore does not cauterize the wound. In the case of the heart this results in immediate supplemental blood flow into the heart muscle into an area surrounding the punch. Animal tests have shown this immediate supplemental blood flow is sufficient to sustain the heart even when a major coronary artery is completely blocked. The procedure may be performed in an open heart surgery method punching cores from the outside of the heart in or may be a percutaneous catheter procedure punching cores from the inside-out. Note that the invention can be used with several organs of the body. The most important organ being the heart and therefore most of the following discussion will be with respect to the heart. Any modification with respect to other organs will be explained at the end of this section.

Figure 1:
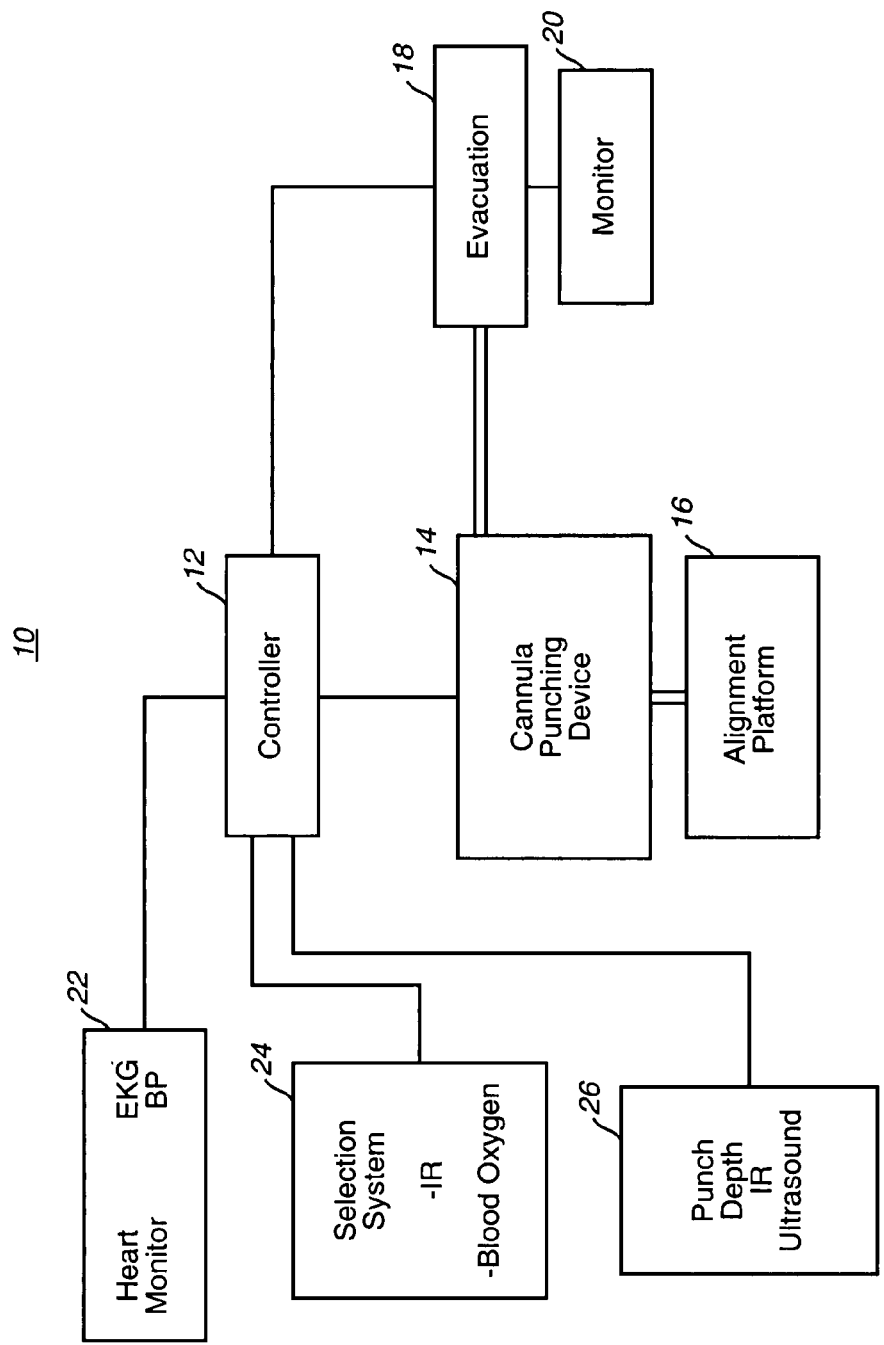
FIG. 1 is a block diagram of a system for providing immediate blood flow to an organ in accordance with one embodiment of the invention.

FIG. 1 is a block diagram of a system 10 for providing immediate supplemental blood flow to an organ in accordance with one embodiment of the invention. The system 10 has a controller 12 that transmits a punching signal to the cannula punching device 14. The cannula punching device 14 is held in place with respect to the heart (organ) by an alignment platform 16. The exact structure of the alignment platform 16 depends on whether procedure is performed in an open-heart surgery method or as a catheter percutaneous procedure. The details of the alignment platform are not important to the present invention. By creating a vacuum, an evacuation system 18 removes the core of the heart muscle and any associated debris generally. A monitoring system 20 determines when the core of the heart muscle has been removed. In one embodiment, this is accomplished by an optical method that determines if blood is flowing through the cannula.

A heart monitor or cardiac rhythm monitor 22 is coupled to the controller 12 and sends a cardiac rhythm signal to the controller 22. The controller 12 uses this information to determine the timing of the punching signal. Since the heart muscle bundles are arranged in a spiral fashion, a channel created at the beginning of contraction will be thin, long, and have a corkscrew shape and therefore may be inadvertently aimed in a direction other than intended. Thus the punching must be timed to coincide with the end of contraction, which results in a short, wide and straight channel. This offers less resistance to the flow of blood from the ventricular chamber into the heart muscle. The heart monitor 22 may be an EKG (electrocardiogram) machine and may also include a blood pressure monitor. A selection system 24 is also coupled to the controller 12 and transmits a punch location information to the controller 12. The selection system 24 may be an infrared sensor or camera or a blood oxygen monitor. Both systems are looking for areas of low blood flow. The IR sensor determines a punch location by first adjusting the temperature of the heart away from ambient (usually cooler) and then as the blood flows through the heart the IR sensor determines areas of the heart that do not return to body ambient temperature as fast. This is an area of low blood flow. The oxygen blood monitor is an optical instrument that looks for areas of low blood oxygen. These are areas of inadequate blood flow in the heart. Note that in one embodiment, the system 10 does not use a selection system. In this case a preset pattern of cores are removed from the heart muscle.

A punch depth selector 26 transmits a punch depth signal to the controller 12. The punch depth selector 26 may be an infrared sensor or an ultrasound sensor. The controller 12 uses this information at the punch location to determine a punch depth of the cannula. The punch depth system may not be necessary in all cases.

Figure 2A:
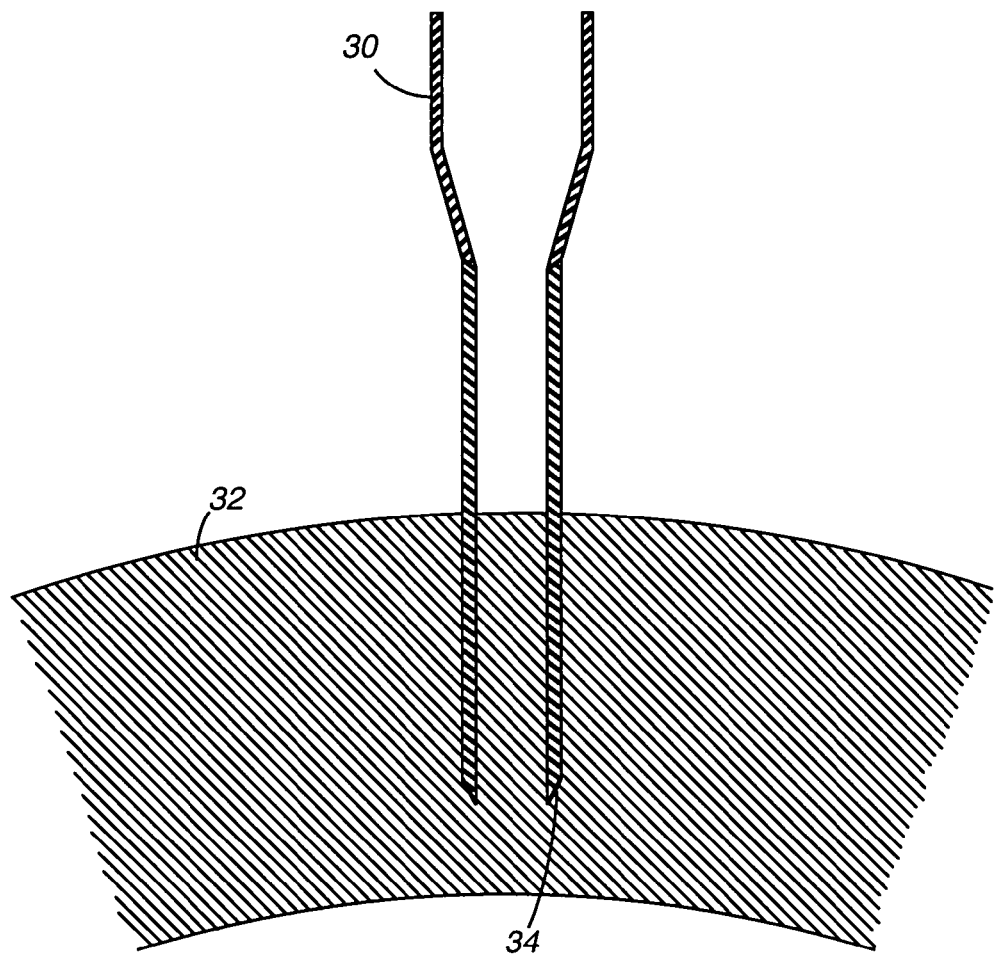
FIG. 2A is a cross sectional view of a cannula inserted into an organ in accordance with one embodiment of the invention.

FIG. 2A is a cross sectional view of a cannula 30 inserted into a organ 32 in accordance with one embodiment of the invention. The cannula 30 has a sharp tip 34 and is usually a cylinder.

Figure 2B:
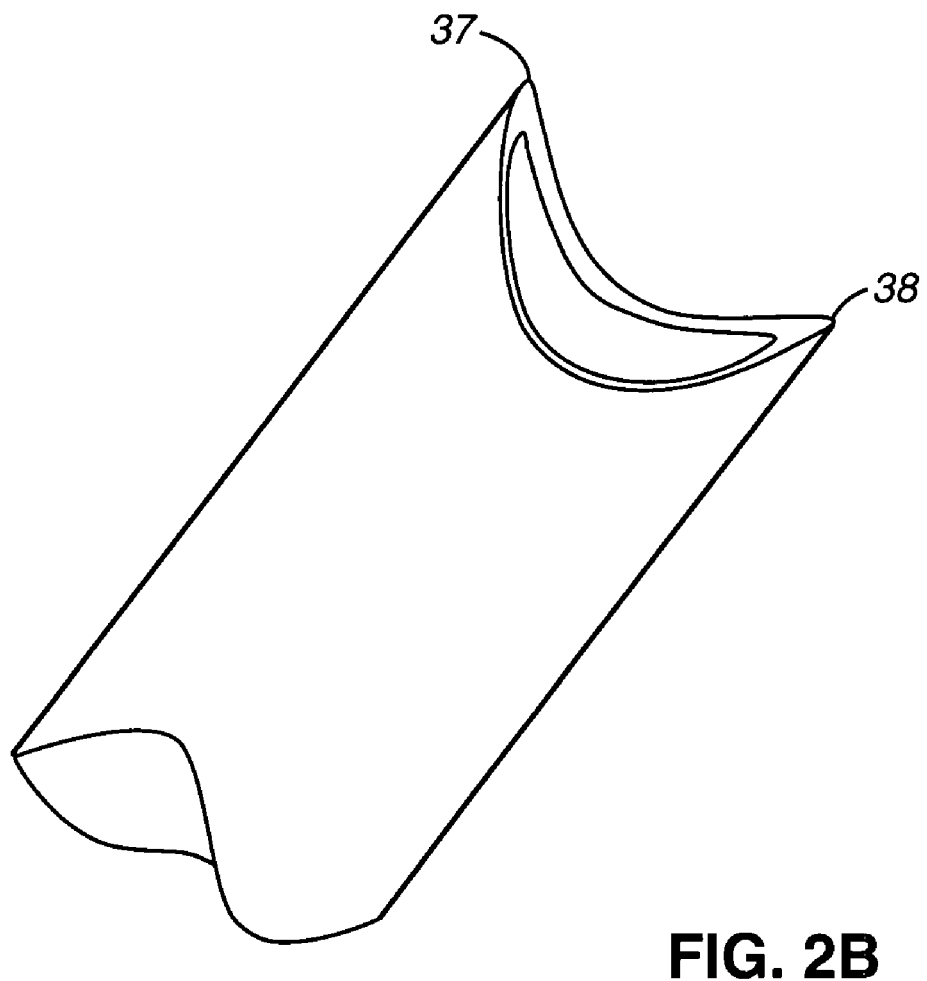
FIG. 2b is close up perspective view of the tip of a cannula in accordance with one embodiment of the invention.

FIG. 2b is a perspective view of cannula 36 that has a plurality of sharpened points 37, 38 at it organ insertion end. When the procedure is performed in an open heart surgery method, the cannula punches all the way through the heart and into the ventricular chamber. The fiborous epicardium, or exterior surface of the heart has a self sealing mechanism that almost immediately seals, and as a result, there is very little blood flow from the heart muscle out of the core. But there is supplemental blood flow from the ventricular chamber into the punch and that is perfused into the heart muscle 32 in an area surrounding the punch.

FIG. 3 is a cutaway view of a percutaneous cannula in accordance with one embodiment of the invention. As stated above the procedure may be performed percutaneously using catheters. In this case it is important that the cannular 40 not punch through the epicardium. As a result, it is necessary to cut the end of the core of heart muscle away so it can be removed. The percutaneous cannula 40 has an outer barrel 42 and an inner rotating barrel 44 and an inner cylinder 46. A rotating blade 48 is connected to the inner rotating barrel 44. The outer barrel 42 has a number of sharp points 50, 52, 54 to reduce the pressure to punch through the myocardium. FIG. 4 is a top left perspective view of a percutaneous cannula 40 in accordance with one embodiment of the invention. This view shows the center blade 56 connect to the outer barrel 42 and having a sharp point 58. FIG. 5 is a top view of a percutaneous cannula 40 in accordance with one embodiment of the invention. This view shows that the rotating blade 48 is stored below the fixed blade 56. FIG. 6 is a top view of a percutaneous cannula 40 in accordance with one embodiment of the invention. This view illustrates how the rotating blade 42 is used to cut the end of the core of heart muscle by rotating 60 under the fixed blade 56. A vacuum crated by the evacuation system 18 is then used to remove the core of the heart muscle. Note that in some percutaneous cases it may only be necessary to create an opening that is just slightly deeper than the myocardium.

Figure 7:
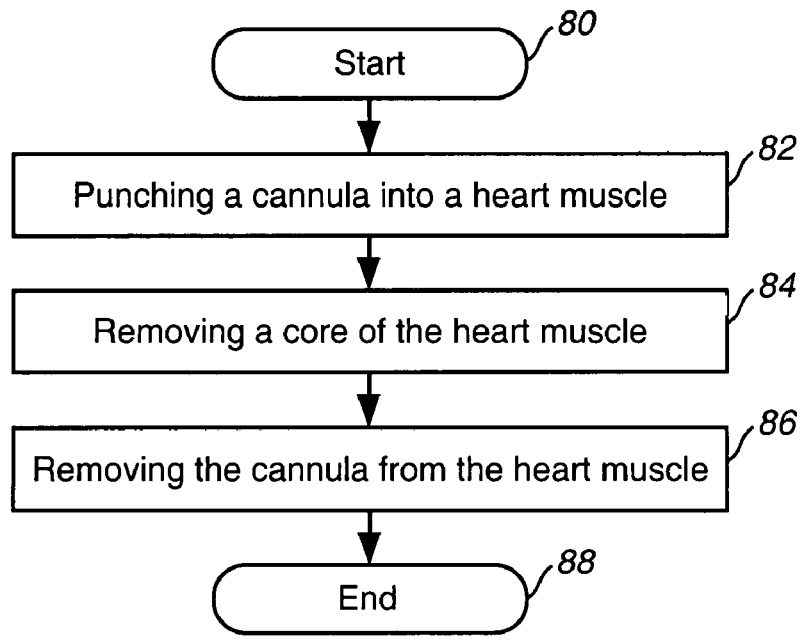
FIG. 7 is a flow chart of the steps used in a method of providing immediate blood flow to an organ in accordance with one embodiment of the invention.

FIG. 7 is flow chart of the steps used in a method of providing immediate supplemental blood flow to an organ in accordance with one embodiment of the invention. The process starts 80 by punching a cannula into a heart muscle at step 82. Next a core of the heart muscle is removed at step 84. The cannula is then removed from the heart muscle at step 86, which ends the process at step 88. Because this process does not generate heat or purposely cauterize the wound, immediate supplemental blood flow is provided to the heart. This is because the heart muscle acts as if it were porous between its fibrous epicardium (external membrane), and it endocardium (internal membrane). It is also believed that overtime this process will also cause revascularization or angioneogenesis, however angioneogensis is not necessary for the process to work. The cannula is not removed until the core of heart muscle has been evacuated through the cannula. In one embodiment, this is sensed by determining that blood is flowing though the cannula. The punching of the cannula is timed to the heart's cardiac rhythm. The process may include determining a punch location. This may be determined by first adjusting the portion of the heart away from ambient and then determining if a location of the heart differs from ambient. As the blood starts to flow into the heart, it will cause the heart's temperature there to move back to body heart ambient temperature. Locations that have low blood flow will remain colder (or hotter) than the areas with more flow. In another embodiment the depth of a punch is determined using ultra sound (ultra sonic echo ranging) involving a computer program.

Figure 8:
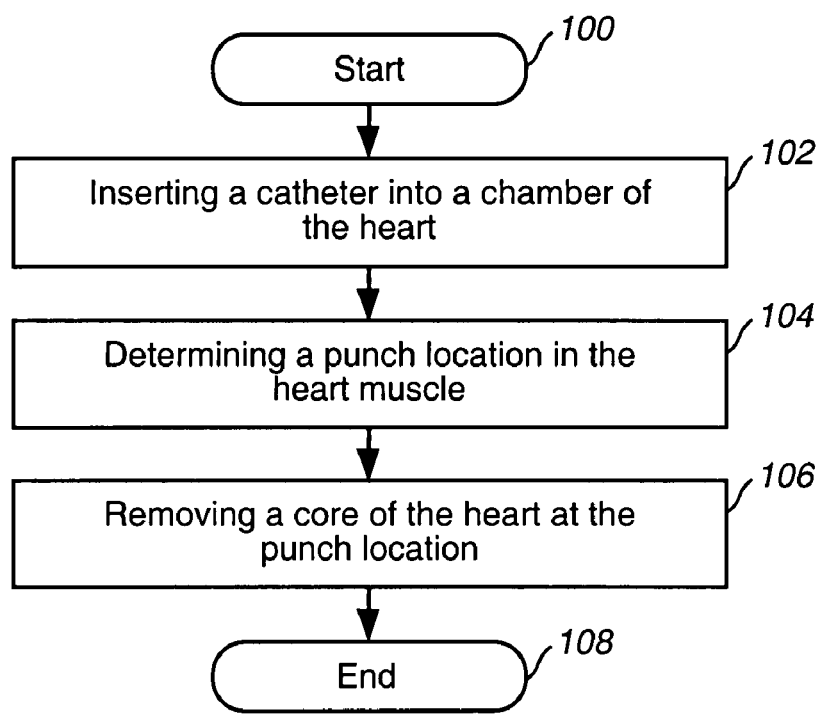
FIG. 8 is a flow chart of the steps used in a percutaneous method of providing immediate blood flow to an organ in accordance with one embodiment of the invention.

FIG. 8 is flow chart of the steps used in a percutaneous method of providing immediate supplemental blood flow to an organ in accordance with one embodiment of the invention. The process starts, step 100, by inserting a catheter into a chamber of the heart at step 102. A punching location in the heart muscle is determined at step 104. A core of the heart is removed at the punch location at step 106, which ends the process at step 108. In one embodiment an angiograph of the heart is first performed. The angiography will tell the physician where there are blockages in the large arteries. Next a catheter is inserted into the artery with the blockage. A ballon is expaned to compress the obstruction against the all of the artery, and a stent is inserted into area of the prior blockage to keep the area open. Cold fluid or blood, serum, etc is then inserted into the artery. Note that warm liquid having temperature above heart ambient temperature could also be used. Then an infrared sensor is used to determine possible areas of low blood flow due to small branch artery obstruction. The infrared sensor may be used inside the ventricular chamber or an exterior infrared sensor may be used. Note that the catheter used for the punching device, which is inside a ventricular chamber will probably be different than the catheter used to place the stent and to insert the cold liquid.

Figure 9:
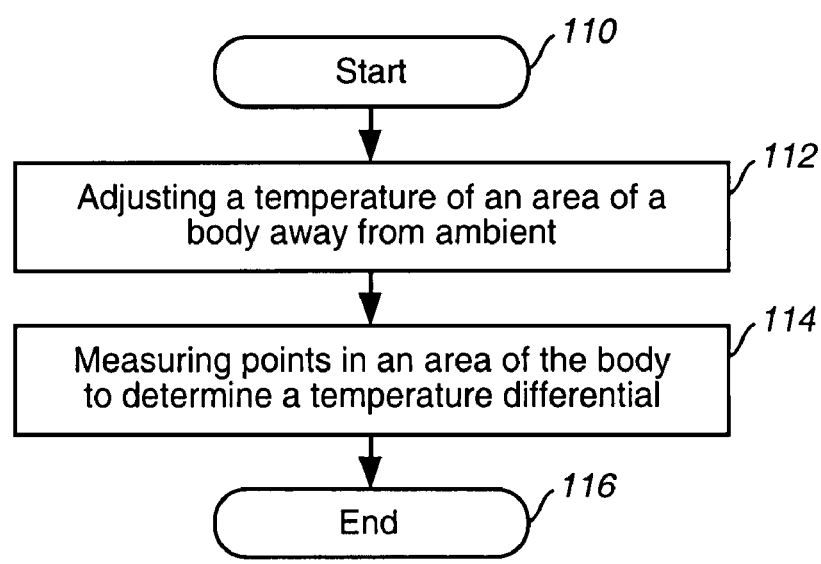
FIG. 9 is a flow chart of the steps used in a method of diagnosing inadequate blood flow to an organ in accordance with one embodiment of the invention.

FIG. 9 is flow chart of the steps used in a method of diagnosing inadequate blood flow to an organ in accordance with one embodiment of the invention. The process starts, step 110, by adjusting the temperature of an area of the body away from ambient at step 112. At step 114, different points of the area of the body are measured to determine a temperature differential which ends the process at step 116. In one embodiment, the temperature is adjusted by interveiniously introducing a non-ambient temperature liquid. Not that the liquid is usually below the body ambient temperature. In another embodiment, the area is imaged by creating a three dimensional infrared image of the area of the body.

Note that in the case where the organ is a kidney, local arterial occlusion can cause the kidney to produce hypertensinogen which is converted by the liver into hypertension and raises the blood pressure. In arteriosclerotic arterial obstructions, where the patient is under age 65 the present procedure is to have kidneys removed. If possible, the arterial flow is re-established, but often the only option is to remove the portions of the kidney that have inadequate blood flow. With IR localization, it is possible to remove the ischemic portions of the kidneys, especially if both kidneys are involved. Ischemic areas of the liver are rare except in liver transplant cases. In all transplants, it is possible that some of the blood vessels may clot despite the efforts of the tissue perfusion teams, and an IR imaging system will show where these areas are. Trauma is an important surgical specialty especially in battlefield trauma where multiple organs may be affected, as well as in the extremities in both trauma and peripheral vascular surgery. Thus this IR imaging system can be used to determine areas of low blood flow due to trauma. Gangrene is another problem that can benefit by this diagnostic technique. The time for a good demarcation method especially in brown recluse spider bites, burns and frost bite, etc. IR imaging can also help determine how much of the bowel to remove in arterial occlusion and the viability of the testicle when the testicle had undergone torsion. In any transplant surgery it is important to ensure that there is adequate blood flow to the transplanted organ. In organs other than the heart it may be necessary to cauterize or suture the entrance of the channel.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

We claim:

1. A method of providing immediate supplemental blood flow to the heart muscle, comprising the steps of:
    punching a cannula from a fibrous epicardium through a heart into a ventricular chamber, by moving the cannula in a straight line, into the ventricular chamber of a heart muscle essentially creating no heat and not cauterizing a wound;
    removing a core of the heart muscle, creating a channel between the ventricle and the heart muscle cells;
    sensing a flow of blood through the cannula; and
    removing the cannula from the heart muscle, wherein immediate supplemental blood flow occurs around a punch location.

2. The method of claim 1, wherein the step of punching creates immediate supplemental blood flow to the heart muscle.

3. The method of claim 1, wherein the step of punching, includes controlling a timing of the punching to the heart's cardiac cycle at the end of systole.

4. The method of claim 1, wherein the step of punching, includes a step of selecting a punching location in the heart muscle.

5. The method of claim 4, wherein the step of selecting includes a step of measuring a temperature of the heart muscle at a location.

6. The method of claim 5, wherein the step of selecting, further includes selecting the location as a punching location, when the temperature at the punch location differs from a heart ambient temperature by a predetermined temperature.

7. The method of claim 5, further including a step of using an infrared sensor to measure the temperature.

8. The method of claim 1, wherein the step of punching includes a step of determining a punch depth.

9. The method of claim 8, further including a step of imaging a punch depth with an ultrasound system.

10. The method of claim 8, further including a step of imaging a punch location with an infrared sensor.

11. The method of claim 1, wherein the step of punching includes selecting the cannula with a punching end that has a point.

12. The method of claim 1, wherein the step of punching includes selecting a punch depth that is less than a thickness of the heart muscle at a punch location.

13. The method of claim 12, wherein the step of removing a core includes a step actvating an end cutter on the cannula.

14. A method of providing immediate supplemental blood flow to the heart muscle, comprising the steps of:
    measuring the temperature of the heart muscle to determine a punch location;
    punching a cannula from a fiborous epicardium through a heart into a ventricular chamber, by moving the cannula in a straight line, into the ventricular chamber of a heart muscle essentially creating no heat and not cauterizing a wound wherein the punching is timed to the heart's cardiac cycle at the end of the systole;
    removing a core of the heart muscle, creating a channel between the ventricle and the heart muscle cells;
    sensing a flow of blood through the cannula; and
    removing the cannula from the heart muscle, wherein immediate supplemental blood flow occurs around the punch location.

\* \* \* \* \*